United States Patent [19]

Price et al.

[11] Patent Number: 5,049,382

[45] Date of Patent: Sep. 17, 1991

[54] COATING AND COMPOSITION CONTAINING LIPID MICROSTRUCTURE TOXIN DISPENSERS

[75] Inventors: Ronald R. Price, Stevensville; Robert F. Brady, Jr., Gaithersburg, both of Md.

[73] Assignee: The United States of America as represented by the Secretary of the Navy, Washington, D.C.

[21] Appl. No.: 343,762

[22] Filed: Apr. 14, 1989

[51] Int. Cl.[5] .................. A61K 37/22; C09D 5/16; C08J 6/00
[52] U.S. Cl. .................. 424/450; 106/18.3; 523/122
[58] Field of Search .............. 523/122; 106/18.3; 424/450

[56] References Cited

U.S. PATENT DOCUMENTS

| | | | |
|---|---|---|---|
| 3,888,176 | 6/1975 | Horai et al. | 106/18.35 |
| 4,098,610 | 7/1978 | Wexell | 106/18.3 |
| 4,241,046 | 12/1980 | Papahadjopoulos | 424/450 |
| 4,385,134 | 5/1983 | Foscante et al. | 523/127 |
| 4,531,975 | 7/1985 | Salome | 106/18.3 |
| 4,751,113 | 6/1988 | Riccio et al. | 427/404 |

FOREIGN PATENT DOCUMENTS

| | | | |
|---|---|---|---|
| 63-25148 | 10/1988 | Japan | 523/122 |
| 8200653 | 3/1982 | PCT Int'l Appl. | 523/122 |

OTHER PUBLICATIONS

Lipid-Based Tubular Microstructures, Schnur et al., vol. 152, p. 181-206 (1987) Thin Solid Films.
Metallization of Lipid Vesicles by Electroless Plating, Ferrar et al., J. Am. Chem. Soc. vol. 110, p. 288-289 (1988).

*Primary Examiner*—Lester L. Lee
*Assistant Examiner*—E. J. Kraus
*Attorney, Agent, or Firm*—Thomas E. McDonnell; Barry A. Edelberg

[57] ABSTRACT

A coating composition contains an effective amount of between 5 and 70 percent by weight of metalized tubules which are or which encapsulate a composition known to have an antifouling effect or known to possess antimicrobial, herbicidal algaicidal or pesticidal (biocidal) properties. When the coating composition is applied to a surface to be protected, a toxic surface environment is formed. The tubules can be used alone or the tubules can contain in the hollow core a secondary or co-biocidal agent or mixtures of these agents. When desired, the metal coating layer metalizing the tubule can be a non-biocidal metal. In those cases, protection is provided by the biocidal agent carried in the core.

23 Claims, No Drawings

COATING AND COMPOSITION CONTAINING LIPID MICROSTRUCTURE TOXIN DISPENSERS

BACKGROUND OF THE INVENTION

1. Field of the Invention

This invention relates to a coating compositions and coatings containing very small copper tubes which can dispense substances toxic to pests. Particularly this invention relates to coatings containing copper or nickel coated lipid tubule microstructures capable of dispensing antimicrobial, algaicidal, herbicidal, pesticidal and mixtures of these compositions to the environment adjacent the coating.

2. Description of the Prior Art

As man constructs artifacts, nature, in the form of weather, microbes and marine life, works to break the artifact down and return it to nature. Since before recorded history, man has applied coatings to artifacts to both beautify and protect the artifact.

Coatings incorporating materials which are aimed at destroying or diverting microbes and marine life are known. The most common coatings are paints used on land based structures of all types and marine coatings used on seaside and seaborne artifacts such as pilings, ship hulls, towers and other structures.

Biological fouling on artifact surfaces such as ship hulls exposed to seawater is a problem which has existed since man first put to the sea. The diversity of fouling organisms and the environments in which they live create complex problems which any useful antifouling coating must overcome. Because these organisms add weight and hydrodynamic drag when they attach to vessels, effective hull fouling control is necessary to minimize fuel consumption, maintain operational speed and maneuverability, and preserve the hull from corrosion.

The schemes to defeat the attachment of drag producing organisms to ships and other man made artifacts almost matches the diversity of the organisms themselves. Any useful biocidal system must be effective against organisms which range from slime-forming bacteria and algae to shell-forming invertebrates with minimal damage to the remainder of the environment.

By definition, biocidal agents are highly toxic to the target species and to other animals and plants as well. The use of highly toxic and environmentally persistent antifoulants such as lead, mercury, arsenic, and cadmium compounds has been discontinued because of environmental degradation. In addition, the highly effective tributyltin compounds have also been banned from use by several state and federal agencies as well as foreign governments because of the detrimental overall impact.

Although in use in one form or another for over a thousand years, the predominant toxicant in use today is copper in the form of copper sulfate, copper hydroxide, cuprous oxide, copper napthenate or copper metal in powder or sheet form. Too great a concentration of copper can also be harmful to the environment. Paints and coatings in use today contain up to 70% by weight of cuprous oxide and release to the environment far more than the minimum effective amount of copper. Of course, the rate of copper release declines exponentially as the coating ages because exposure of the paint to the environment leaches active toxins until the paint is no longer effective.

Although now the toxin of choice, copper is an environmental hazard which is toxic to invertebrate and vertebrate marine organisms which include many economically valuable species such as oysters and clams, fish and seaweed. The release of copper to the environment must be carefully controlled. In addition, if large quantities are inhaled or ingested during hull repainting, copper oxide can be a hazard for dockyard workers. In contained waters which are frequented by large ocean-going vessels, such as the Suez Canal, the water quality has deteriorated because of high levels of copper. Paints which release high levels of copper may soon be restricted by environmental regulation.

Many inventors have tried to find a way of balancing the beneficial against the detrimental effects of releasing copper or other agents to prevent microbial or marine fouler action adjacent a treated surface. U.S. Pat. No. 4,098,610 describes a biocidal glass additive for marine paints which slowly releases copper. U.S. Pat. No. 4,129,610 describes a water soluble coating for ships which slowly releases copper. Another slow toxin release scheme is described by Foscante et al. in U.S. Pat. No. 4,385,134 where a polymer is used as the slow release agent. Other marine anti-fouling paints and coatings are described in U.S. Pat. Nos. 4,480,011; 4,594,365; 4,602,011. U.S. Pat. No. 4,531,975 describes a marine coating which uses hollow glass bead microspheres or balloons to thicken and change the coating's density.

The mechanisms and history of antifouling paints as well as a discussion of the problems with ablative or erodible type dispensing coating can be found in Foscante et al. U.S. Pat. No. 4,670,481. Foscante describes a paint incorporating tributyltin.

A deficiency in soft ablative paints and in some of the harder leaching paints is rapid mechanical erosion caused by flowing seawater. Often erosion of the coating in the bow, skegs, struts, and keel sections of the ship is more rapid than that in large flat surfaces. Paint is removed quickly from those areas, and the underlying hull is exposed to the ravages of marine fouling agents.

Coatings or paints which incorporate particles of copper or similar materials have the added problem that erosion of the ablative coating surrounding the particle can result in the sudden release of the particle and loss of its benefits. Thus without rational control of the leaching of toxicant from the coating, premature release of large amounts of the biocide in a dropped particle pollutes the environment and reduces the long term performance of marine antifouling paint.

Other problems are present when secondary or auxiliary toxins are used. Secondary toxin materials cannot be effective in promoting extended service lifetimes of conventional coatings unless these highly soluble materials can be protected from rapid leaching and chemical breakdown. Regardless of the myriad schemes developed to release copper and other toxins slowly, the problems of controlled slow release have not been solved.

The need for slow release of biocidal and pesticidal agents is not restricted to a marine environment. In many land environments, mold and other microbial and insect pests attack houses, vehicles and other land based artifacts. Copper and other toxic materials are incorporated into paints coatings and roofing material to suppress or destroy pest activity. U.S. Pat. Nos. 3,894,877; 3,888,683; 3,888,682; and 3,888,176 are all directed at incorporating algaicidal materials into roofing products. Land based artifacts suffer ablative wear similar to sea borne artifacts. A constant exposure of fresh toxic material is needed to protect the coated surface from microbial or pest infestation.

As described in U.S. Pat. No. 3,318,697, it is known to metal coat lipid and wax globules. For pharmaceutical and other purposes, it is known to incorporate materials inside a waxy globule or a liposome. A special kind of liposome form, known as a tubule, was invented at the Naval Research Laboratory. These tubules are hollow tube-shaped microstructures fabricated by self organization of polymerizable diacetylenic phospholipid molecules. Morphologically, tubules are cylinders analogous to soda straws with diameters of approximately 0.5 $\mu$m and lengths from 1 to over 200 $\mu$m. The preparation of tubules is discussed in an article by Schnur et al. LIPID-BASED TUBULE MICROSTRUCTURES, Thin Solid Films, 152, p. 181–206,(1987) and the articles cited therein. That same article, in which one of the inventors is a co-author, also describes metal coating tubules and using them as "microvials" to "entrap, transport and deliver polymeric reagents to a desired site." see page 200.

Each of the ablative or erodible materials of the prior art tend to dispense particles of material to the environment which causes an uneven and sometimes overly high concentrations of the toxic material. In addition, the agent to be dispensed often reduces or weakens the integrity of the coating. The problems of the ablative coating have not been fully solved.

SUMMARY OF THE INVENTION

Accordingly, it is an object of this invention to have an antimicrobial, algaicidal, herbicidal, and pesticidal (generically referenced to as biocidal) coating which will slowly dispense biocidal material to the environment adjacent the coating.

Another object of this invention is a biocidal coating in which the toxic material strengthens the coating.

An additional object of the invention is a coating composition dispensing controlled amounts of copper to the environment at an acceptable rate to meet industry and regulatory agency standards.

Yet another object of the invention is a coating which can dispense controlled amounts of other secondary or additional biocidal materials together with copper.

A further object of this invention is a composition which forms a coating capable of the controlled slow release of toxic agents.

These and additional objects of the invention are accomplished by incorporating into a coating composition an effective amount of between 5 and 70 percent by weight of metalized tubules which have a composition known to have an antifouling effect or known to possess antimicrobial, herbicidal algaicidal or pesticidal (biocidal) properties. When the coating composition is applied to a surface to be protected, a toxic surface environment is formed. The tubule can be used alone or the tubules can contain in the hollow core a secondary or co-biocidal agent or mixtures of these agents. When desired, the metal coating layer metalizing the tubule can be a non-biocidal metal In those cases, protection is provided by the biocidal agent carried in the core.

DESCRIPTION OF THE PREFERRED EMBODIMENTS

A controlled rate of release of a toxicant from the surface of a coating can be achieved by creating a porous structure of controlled dimensions within a coating. The toxicant must migrate through the coating to reach the outer environment. This structure can be created by adding to a coating vehicle an effective amount of between five and seventy percent of long, thin, hollow tubules which contain or are composed of a biocidal toxicant.

The composition of the coating, and hence its characteristic rate of ablation, can be controlled by the concentration and type of the binder resins in the coating, the composition and type of the ablative resin or filler, if any, and the relative hardness of the coating. The rate of release of the toxicant can be further controlled by the loading of the tubules in the vehicle, the concentration of toxicant contained in the tubules, the dimensions of the tubules (material diffuses into the environment through a gradient), and solubility modifiers within the encapsulated co-toxicant. The biocidal toxicant is chosen during the manufacture of the tubules, and its rate of release can be further modified during encapsulation by the addition of solubility modifiers such as glues, resins, polymers and other "slow release agents".

The tubules can be metalized with any metal capable of being plated. It is preferred that the tubules be made of copper, but nickel may be used in some applications. The copper as well as other metals can be in pure form or can be alloyed such as copper with zinc or other metals to improve or enhance the toxicity.

The preferred size of the tubules are from 1 to 1000 microns in length and from 0.1 to 1 microns in diameter. The tubules can be of any source of manufacture but it is preferred that these tubules be metalized lipid tubules because such tubules can be consistently formed to uniform dimensions in the desired size range.

Hollow tubules are formed from diacetylinic phosphatidylcholine by several different techniques such as heating the lipid above the phase transition temperature and then slow cooling the lipid to form the tubules. Alternatively, the tubules can be formed by heating the lipid above the phase transition temperature, rapidly cooling the lipid to about 0° C., raising the temperature above the phase transition temperature a second time and slowly cooling it to room temperature.

Preparation of starting materials and tubules is described in detail in several articles published by personnel of the Naval Research Laboratory (NRL). These procedures, which are incorporated herein by reference, are summarized and described in the article by Schnur et al., Lipid-Based Tubule Microstructures, Thin Solid Films, 152, pp. 181–206 (1987) at pp. 183–186.

Tubules are delicate and can be easily destroyed. It has been found that these tubules act as an excellent template which can be uniformly and continuously coated with metal either on one surface or, more preferably, on both surfaces. The most preferred metalization technique is electroless plating described in detail in the above referenced Schnur et al. article at pp. 198–200. The metal coating on the metalized tubules is of uniform thickness of about 20 nm both inside and outside the hollow tubule. The preferred coating is between about 20 nm and 2000 nm.

Once coated with metal, the tubules are filtered to remove the solvent and are air dried to a powder form. At this point the tubules can be stirred into the coating vehicle by gentle agitation. If the tubules are processed to a wet stage and then solvent exchanged with a coating compatible solvent, the tubules can be mixed directly into the coating with the diluent solvent.

When exposed to an environment such as the ocean or atmosphere, natural chemical reactions will begin to interact with the copper coating on the tubule wearing away minute quantities of pure copper or converting the copper to oxides. Both copper and its oxides are toxic to target pests and are dispensed to the environment at a relatively predictable and uniform rate because of the uniformity of the metal coating. Of course, the rate at which the copper or copper compound dissolves is controlled by the solubility rate in the environment. These rates are easily calculable once the environment is known (eg. salt vs. fresh water).

The small copper or copper and zinc coated tubules are an excellent anti-microbial or pesticidal agent by themselves. The toxic potential of the tubules can be increased by incorporating a secondary or co-biocidal agent into the tubule. As noted by Schnur et al., the tubules can act as microvials. These micro vials can be filled by a variety of techniques including capillary action.

In the preferred embodiments of the invention the tubules are filled with an antifouling and antimicrobial agent such as tetracycline. Many organisms create an environment attractive to free swimming marine larva. By creating an environment which is inhospitable to these organisms fouling by free swimming larva is reduced or eliminated. The types of materials which can be incorporated into the tubules to create inhospitable environment are bactericides, herbicides, molluskicides, insecticides, pesticides all generically refered to as biocides.

It is preferable to retard the discharge of the co-toxicant once it is incorporated or encapsulated into the tubule so that the incorporated material is not instantly discharged on contact with an aqueous environment. This retardation can be accomplished by several methods. First, the chemical compounds used can be of limited solubility in water. Second, organic materials of low solubility, such as musculagenous binders like fish glues (one example could be LePage fish glue), cellulose, polypeptide polymers, or inorganic materials such as ceramics or silanes could be used as binders. A further method would be to dissolve the compound in a monomeric material which could be polymerized once in place in the tubule lumen, preferably of equal solubility to the ablative binder. The ideal solubility modifier would have a rate of dissolution which would compliment that of the metallic coating and the ablative binder. Such polymers could be selected from epoxies such as the Dow Corning DER series of resins or the Shell Epon series of resins, an acrylate resin such as methyl or hydroxymethyl methacrylate, a urethane resin or the like. Some of the urethanes themselves have fungicidal or pesticidal properties which can add to the total effect of our invention.

Alternatively, it has been found that the paint medium can penetrate into the tubule. If the tubule is loaded with a co-toxicant material, the paint might soak into the end regions of the tubule and aid in controlling the access of water to the material. Once cured in place, the co-toxicant will be incorporated into the paint in such a manner that it will ablate or dissolve at a controlled rate which provides an excellent slow toxin dispensing coating. Preferably the ablative or dissolution rate of the binder, metal coated tubule and filler will be substantially the same.

Tubules which have been electroless plated with a copper metal layer or other metals known to have antifouling properties can be dispersed in a wide variety of organic binders. Once the matrix material of the coating cure, the tubules form a trabecular network within the body of the coating. This network when left hollow acts as a capillary for seawater or rainwater. When filled, the pore size of the tubules and the solubility of the encapsulated secondary toxicants controls the release of included toxicants within the vehicle. Copper ions are released from the metallic coating of the tubules and diffuse through the channels to the surface of the coating.

The hardness and ablation rate of the coating, such as paint, is controlled by the selection of the resins used as the coating vehicle. Such as vinyl-rosin mixtures, acrylics, polyurethanes, and epoxies have been used successfully for this purpose. If some property of the coating can be made to respond to the local environment, such as barnacle basal plate intrusion into the coating body, then the actual release of toxicant is limited to such areas. In addition, by use of polypeptide coating binders, it is possible to use the actual release of protease by fouling organisms as the stimulus to expose subsurface tubules and initiate localized toxicant release.

Further control of the coating properties and the release rates of the toxicants can be controlled by the orientation and distribution of the tubules by two methods. First orientation can be accomplished by coating the surface in the presence of a magnetic or electrical field which creates a preferred orientation of the tubules to the coated surface, either parallel or normal. In addition, in coatings where the film thickness is less than the average tubule length, the tubules can be oriented parallel to the surface.

Because of the aspect ratio and size of the tubules, the tubules can further act to form, within the coating, a network which adds improved physical characteristics. At the least the tubules extend down into the surface so that they are anchored in place. This ability to form a composite structure within the coating reduces the amount of wasted copper that drops out of the coating rather than dissolving in place.

The tubules are effective antifouling agents in any organic binder. Such organic resins such as acrylics, epoxies, polyurethanes, vinyls, rosins or mixtures of these may be used. The most preferred coating compositions are acrylic copolymers, epoxies and vinyls.

Having described the invention, the following examples are given to illustrate specific applications of the invention including the best mode now known to perform the invention. These specific examples are not intended to limit the scope of the invention described in this application.

EXAMPLE

The tubules are formed and metalized with electroless coating by methods described in Schnur et al. Once formed, the tubules are rinsed free from any residual lipid material or electroless plating bath chemicals in water. The tubules are then added to a saturated solution of the co-toxicant tetracycline and binder and allowed to dwell in this solution for a time sufficient to allow for the complete diffusion of the solution through the lumen of the tubule. Following this the tubules are allowed to settle out and the excess solution is removed. The tubules and the contained materials are allowed to dry and are then mixed into the coating prepared by I mixing the following materials in the proportions by weight indicated.

Example 1

| | |
|---|---|
| Polyvinyl resin (VYHH by Union Carbide) | 10% |
| Polyvinylbutryl Resin (Monsanto) | 5% |
| Polyvinyl Acetate Resin (Monsanto) | 1% |
| Methyl Isobutyl Ketone | 25% |
| Xylene | 30% |
| Copper Tubules Containing Tetracycline | 10% |
| Zinc Oxide (Fisher Scientific) | 9% |
| Molybdenum Disulphide (Climax) | 10% |

The vinyl resins are dissolved in the methyl isobutyl ketone and diluted with the xylene too form a solution of resin in solvent. The zinc oxide is added and followed by the addition of the tubules and molybdenum disulphide. This forms a Navy gray colored coating. The resulting mixture is painted onto primed steel panels for testing.

Example 2

The coating composition is formed by mixing the following constituents in the proportions by weight indicated:

| | |
|---|---|
| Vinyl resin (e.g. VYHH by Union Carbide) | 55 |
| Rosin (e.g., R-307 by Fisher Scientific) | <200 |
| Tricresyl Phosphate, (e.g. T-342 by Fisher) | 50 |
| Methyl Isobutyl Ketone | 165 |
| Xylene | 115 |

To 970 parts by weight of the above mixture is added 61 to 150 parts by weight of copper tubules containing tetracycline. The mixture is stirred to wet and disperse the tubules and the resulting mixture is painted onto primed steel panels for testing.

Example 3

Copper plated tubules containing tetracycline or Dowicide are added at a rate of 10 to 40 percent by weight to a copolymeric system such as acrylic or methacrylic ester monomers such as those described in U.S. Pat. No.4,687,792 included herein by reference. This coating serves as a self ablative antifouling paint.

Example 4

Tubules containing a secondary toxicant material such as Tetracycline are incorporated into an epoxy resin vehicle as follows. Figures are in parts by weight

| | |
|---|---|
| Epoxy Resin (e.g. Shell Epon 828) | 60 |
| Versamid 140 (Henkel) | 40 |
| Zinc Oxide | 10 |
| Copper Tubules and Secondary Toxicant | 10 to 70 |
| Xylene | 150 |

The tubules are added to the Epon 828 along with the zinc oxide powder and dispersed. The mixture is diluted with the solvent and mixed with the versamid curing agent just prior to use.

Example 5

A coating is formed from a partly cured (tacky) epoxy or urethane resin which has been applied to the surface to be protected. To this tacky coating is applied a layer of copper coated tubules containing secondary co-toxicant materials consisting of antibiotics, herbicides, molluskicides, or pesticides suitable for use as antifouling toxicants. This layer is applied by blowing a dry powder preparation of the tubules containing a co-toxicant onto the partly cured coating and allowing it to harden, thus forming an adhesive bond to the toxicant and exposing the toxicant to the environment.

The above mixtures are applied to a surface by roller, brush or spray over a suitable primer or barrier coating. The tubules are easily dispersed into the paint vehicle and may be applied by means commonly used in the application of paint coatings. The coating compositions are applied to steel panels over an epoxy primer coating. Two coats are applied by brush to form the paint film for testing.

After the coating has cured, the panels are suspended in a marine environment. Following immersion, the panels are removed and examined periodically for evidence of marine growth or coating failure.

Following a nine month test exposure of the panels in the marine environment the results are as follows. On the test panel coated with vinyl paint as in example 1 the panel remained clear of hard fouling completely when the tubules were added at a rate of 10% by weight containing tetracycline. At 5% loading by weight, the surface of the panel exhibited fouling over less than 5 percent of the surface. In both cases soft fouling was easily removed by soft brush.

This invention provides an improvement over prior art in the use of the novel size and shape of the tubules to control environmental, particularly seawater, penetration into the coating in place of or in addition to a leaching component such as rosin which is very sensitive to temperature and mechanical and chemical erosion. Also, the invention forms a short fiber reinforcement within the coating, the metal coated tubule prevents the premature loss of large quantities of still active concentrated toxicants. In addition, the invention encapsulates and protects secondary toxicant materials such as tetracycline which would otherwise be removed from the coating by water penetration, often prior to the desired time.

In addition to toxicants, the tubules can contain and distribute secondary toxicant materials such as anti-corrosion compounds or surface drag reduction agents. These improvements reduce the need for large quantities of metallic toxicants in antifouling coatings and lengthen the service life and operational flexibility of vessels or devices which utilize such coatings.

Obviously, many modifications and variations of the present invention are possible in light of the above teachings. It is therefore to be understood that, within the scope of the appended claims, the invention may be practiced otherwise than as specifically described.

We claim:

1. A biocidal coating composition comprising:
a coating carrier; and
cylindrical microstructures formed upon lipid tubule templates, said cylindrical microstructures having a hollow core and an inner cylindrical surface metalized with a layer of a biocidal metal, said cylindrical microstructures being present in said carrier in a concentration effective to provide said coating with biocidal activity.

2. The composition of claim 1 wherein the thickness of the metalized layer is between approximately 20 nm to 2000 nm.

3. The composition of claim 2 wherein the inner and outer cylindrical surfaces of said hollow cylindrical microstructures are metalized.

4. The composition of claim 3 wherein the metal of the metalized layer is selected from the group consisting of copper, nickel, mixtures of these metals and alloys of each of these metals.

5. The composition of claim 4 wherein the metalized layer is copper or its alloys.

6. The composition of claim 5 wherein the hollow core is filled with at least one additional biocidal agent.

7. The composition of claim 4 wherein the metalized layer is nickel or its alloys.

8. The composition of claim 7 wherein the hollow core is filled with at least one additional biocidal agent.

9. The composition of claim 8 wherein the biocidal agent is a molluskicide.

10. The composition of claim 6 wherein the biocidal agent is selected form the group consisting of pesticides, algicides, herbicdes, and mixtures of these.

11. The composition of claim 10 wherein the carrier is a paint.

12. The composition of claim 10 wherein the carrier is a marine coating.

13. A biocidal coating composition comprising:
    a coating carrier; and
    cylindrical microstructures formed upon lipid tubule templates, said cylindrical microstructures having a hollow core with an inner cylindrical surface metalized with a layer of metal, said hollow core having a filling of at least one biocidal agent other than said metal, said cylindrical microstructures being present in said carrier in a concentration effective to provide said coating with biocidal activity.

14. The composition of claim 13 wherein the biocidal agent is selected form the group consisting of pesticides, algicides, herbicides, molluslicides and mixtures of these.

15. The composition of claim 14 wherein the biocidal agent is tetracycline.

16. A biocidal coating composition on a structural substrate, said biological coating composition comprising:
    a coating carrier; and
    cylindrical microstructures formed upon lipid tubule templates, said cylindrical microstructures having a hollow core and having an inner cylindrical surface metalized with a layer of biocidal metal, said cylindrical microstructures being present in said carrier in a concentration effective to provide said coating with biocidal activity.

17. The composition of claim 16 wherein the metal of the metalized layer is selected from the group consisting of copper, nickel, mixtures of these metals and alloys of each of these metals.

18. The composition of claim 17 wherein the thickness of the metalized layer is between approximately 20 nm to 2000 nm.

19. The composition of claim 18 wherein the inner and outer cylindrical surfaces of said hollow cylindrical microstructures are metalized.

20. The composition of claim 19 wherein the hollow core is filled with at least one additional biocidal agent selected form the group consisting of pesticides, algicides, herbicides, and mixtures of these.

21. The composition of claim 20 wherein the metalized layer is copper or its alloys.

22. The composition of claim 20 wherein the metalized layer is nickel or its alloys.

23. The composition of claim 22 wherein the biocidal agent is a molluskicide.

* * * * *